US009472180B2

(12) United States Patent
Olsson

(10) Patent No.: US 9,472,180 B2
(45) Date of Patent: Oct. 18, 2016

(54) HEADSET AND A METHOD FOR AUDIO SIGNAL PROCESSING

(71) Applicant: GN Netcom A/S, Ballerup (DK)

(72) Inventor: Rasmus Kongsgaard Olsson, Roskilde (DK)

(73) Assignee: GN Netcom A/S (DK)

( * ) Notice: Subject to any disclaimer, the term of this patent is extended or adjusted under 35 U.S.C. 154(b) by 64 days.

(21) Appl. No.: 14/566,959

(22) Filed: Dec. 11, 2014

(65) Prior Publication Data

US 2015/0170632 A1 Jun. 18, 2015

(30) Foreign Application Priority Data

Dec. 13, 2013 (EP) .................................... 13197139

(51) Int. Cl.
*A61F 11/06* (2006.01)
*G10K 11/16* (2006.01)
(Continued)

(52) U.S. Cl.
CPC ......... *G10K 11/175* (2013.01); *G10L 21/0208* (2013.01); *H04R 1/1091* (2013.01);
(Continued)

(58) Field of Classification Search
USPC ........................................................ 381/71.6
See application file for complete search history.

(56) References Cited

U.S. PATENT DOCUMENTS

2004/0175008 A1 9/2004 Roeck et al.
2011/0129097 A1 6/2011 Andrea (Continued)

FOREIGN PATENT DOCUMENTS

WO WO 2007/137364 5/2007
WO WO 2007/137364 12/2007

(Continued)

OTHER PUBLICATIONS

Harvey Dillon; "Hearing Aids, chapter 7, Advanced signal processing schemes for hearing aids", In: "Hearing Aids", Jan. 1, 2001, Thieme, XP055117484, ISBN: 978-1-58-890052-4, pp. 187-208.
Vanden Berghe Jeff et al: "An Adaptive noise canceller for hearing aids using two nearby microphones", The Journal of the Acoustical Society of America, American Institute of Physics for the Acoustical Society of Amercia, Ne York, NY, US, col. 103, No. 6, Jun. 1, 1998, pp. 3621-3626-, XP012000334, ISSN: 0001-4966, DOI: 10.1121/1.423066.

(Continued)

*Primary Examiner* — Quynh Nguyen
(74) *Attorney, Agent, or Firm* — Altera Law Group, LLC

(57) ABSTRACT

A headset and a method configured to process audio signals from multiple microphones, comprising: a first pair of microphones (101,102) outputting a first pair of microphone signals and a second pair of microphones (103, 104) outputting a second pair of microphone signals; a first near-field beamformer (105) and a second near-field beamformer (106) each configured to receive a pair of microphone signals and adapt the spatial sensitivity of a respective pair of microphones as measured in a respective beamformed signal ($X_L$; $X_R$) output from a respective beamformer (105; 106); wherein the spatial sensitivity is adapted to suppress noise relative to a desired signal; a third beamformer (107) configured to dynamically combine the signals ($X_L$; $X_R$) output from the first beamformer (105) and the second beamformer (106) into a combined signal ($X_C$); wherein the signals are combined such that signal energy in the combined signal is minimized while a desired signal is preserved; and a noise reduction unit (109) configured to process the combined signal ($X_C$) from the third beamformer (107) and output the combined signal such that noise is reduced.

13 Claims, 3 Drawing Sheets

(51) Int. Cl.

| | |
|---|---|
| ***H03B 29/00*** | (2006.01) |
| ***G10K 11/175*** | (2006.01) |
| ***H04R 3/00*** | (2006.01) |
| ***H04R 1/10*** | (2006.01) |
| ***G10L 21/0208*** | (2013.01) |
| *H04R 1/40* | (2006.01) |
| *G10L 21/0216* | (2013.01) |

(52) U.S. Cl.

CPC .... *H04R 3/005* (2013.01); *G10L 2021/02166* (2013.01); *H04R 1/406* (2013.01); *H04R 2201/10* (2013.01); *H04R 2201/107* (2013.01)

(56) References Cited

U.S. PATENT DOCUMENTS

2012/0020485 A1* 1/2012 Visser .................... H04R 3/005 381/57
2014/0093093 A1* 4/2014 Dusan .................... H04R 3/005 381/74

FOREIGN PATENT DOCUMENTS

| | | |
|---|---|---|
| WO | WO 2010/022456 | 3/2010 |
| WO | WO 2010/051606 | 5/2010 |
| WO | WO 2011/101045 | 10/2010 |
| WO | WO 2013/030345 | 3/2013 |

OTHER PUBLICATIONS

Extended European Search Report dated May 22, 2014 for European Patent application No. 13197139.2.

Philip Winslow Gillett: "Head Mounted Microphone Arrays", Aug. 27, 2009, XP055183072, Blacksburg, Virginia: Retrieved from the Internet: URL:http://scholar.lib.vt.edu/theses/available/ etd-09042009-104511/ [retrieved on Apr. 15, 2015].

Bolls F: "Suppression of Acoustic Noise in Speech Using Spectral Subtraction", IEEE Transactions on Acoustics, Speech and Signal Processing, IEEE Inc. New York, USA, vol. 27, No. 2,Apr. 1, 1979, pp. 113-120, XP000560467, ISSN: 0096-3518, DOI: 10.1109/ TASSP.1979.1163209.

Laugesen S et al: "Design of a microphone array for headsets", Applications of Signal Processing to Audio and Acoustics, 2003 IEEE Workshop on. New Paltz, NY, USA Oct. 19-22, 2003, Piscataway, NJ, USA, IEEE, Oct. 19, 2003, pp. 37-40, XP010696436, DOI: 10.1109/ASPAA.2003.1285803; ISBN: 978-0-7803-7850-6.

Vandenberghe Jeff et al: "An adaptive noise canceller for hearing aids using two nearby microphones", The Journal of the Acoustical Society of America, American Institute of Physics for the Acoustical Society of America, New York, NY, US, val. 103, No. 6, Jun. 1, 1998, pp. 3621-3626, XP012000334, ISSN: 0001-4966, DOI: 10.1121/1.423066.

Extended European Search Report dated May 4, 2015 for European Patent app No. 14197611.8.

* cited by examiner

HEADSET AND A METHOD FOR AUDIO SIGNAL PROCESSING

It has been discovered that use of multiple microphones and the use of beamforming techniques provide audio signal reproduction that is superior to single microphone or non-beamforming systems. The multiple microphones are located at different positions and allows so-called spatial sampling which in turn enables cancelling of noise interfering with a desired signal such as a person's voice; this is also known as beamforming, spatial filtering or noise-cancelling. Subsequent time varying post-filters are often applied as a means to further discriminate the person's voice from (background) noise signals.

Multiple microphones and the use of beamforming techniques are frequently embodied in headsets, hearing aids, laptop computers and other electronic consumer devices.

The technical field of beamformers has been extensively researched; however their qualities and configurations have not been fully exploited.

RELATED PRIOR ART

US 2012/0020485 discloses an audio signal processing method which estimates a first indication of a direction of arrival, relative to a first pair of microphones, of a first sound component received by the first pair of microphones; and estimates a second indication of a direction of arrival, relative to a second pair of microphones, of a second sound component received by the second pair of microphones. The first and the second pair of microphones are arranged at respective sides of a person's head during normal operation of a device using the method. The method also involves controlling gain of an audio signal to produce an output signal, based on the first and second direction indications.

SUMMARY

There is provided an apparatus, such as a headset, configured to process audio signals from multiple microphones, comprising: a first pair of microphones outputting a first pair of microphone signals and a second pair of microphones outputting a second pair of microphone signals; wherein the first pair of microphones are arranged with a first mutual distance and the second pair of microphones are arranged with a second mutual distance, and wherein the first pair of microphones are arranged at a distance from the second pair of microphones that is greater than the first mutual distance and the second mutual distance at least when the apparatus is in normal operation; a first beamformer and a second beamformer each configured to receive a pair of microphone signals and adapt the spatial sensitivity of a respective pair of microphones as measured in a respective beamformed signal output from a respective beamformer; wherein the spatial sensitivity is adapted to suppress noise relative to a desired signal; a third beamformer configured to dynamically combine the signals output from the first beamformer and the second beamformer into a combined signal; wherein the signals are combined such that noise energy in the combined signal is minimized while a desired signal is preserved; and a noise reduction unit configured to process the combined signal from the third beamformer and output the combined signal such that noise is reduced.

Thus, beamforming is provided in a first beamforming stage with the first beamformer and the second beamformer processing the microphone signals and in a second stage with a third beamformer processing signals output from the first stage. The first beamforming stage serves to enhance or emphasize the desired signal locally with respect to the microphone pairs by adapting the spatial sensitivity of a respective microphone pair. The spatial sensitivity is adapted, e.g., by adjusting beamformer coefficients to control the spatial configuration of the beamformer nulls which may comprise adjusting beamformer coefficients such that the beamformer obtains an omni-directional characteristic, which is useful to avoid amplification of uncorrelated (between microphones) noise such as wind noise. The effectiveness of the first beamforming stage depends on the assumption that the microphones of each microphone pair are situated closely to one another (for reasons explained below).

In addition to such local optimization in capturing a desired signal, the level of the noise component may vary considerably between the first and second beamformed signals. This may be due to different levels at the microphones, e.g., wind turbulence is a highly local phenomenon, and acoustic shadowing effects from the user's head in a head worn device. Furthermore, the first and the second beamformers may not be able to cancel the noise equally well, depending on the relative position of the microphone pair, the signal of interest and interfering noises.

The third beamformer is thus configured to receive signals that have already been subject to local optimization by the first stage beamformers whereby the desired signal is isolated as far as possible. By dynamically combining signals from the left-hand side and the right-hand side, it is possible to select or emphasize a spatially controlled signal from the most favourably positioned microphone pair.

Processing microphone signals in this way, improves the effect of noise suppression by the noise reduction unit when, as claimed, it is configured to process the combined signal from the third beamformer. This is partly ascribed to the observation that desired signals stands out clearer after such a two-stage beamforming and thereby makes noise suppression more effective. Furthermore, the two-stage beamformer approach achieves the combined benefit of beamforming on microphones that are closely spaced and microphones that are not closely spaced using well known dual-microphone beamformers. The third beamformer may combine its input signals by linear or non-linear weighing of the input signals.

The apparatus, such as a headset, a hearing aid or another apparatus picking up audio signals by means of microphones may be configured to be worn by a person with the first pair of microphones arranged on a left-hand side of a person's head and the second pair of microphones arranged on the right-hand side of the person's head. Typically, the two pairs of microphones are sitting on an ear-cup of a headphone, a spectacle frame or booms or other protrusions at respective sides of a person's head. The microphones are arranged, at least approximately, in a so-called end-fire configuration. The microphones may alternatively or additionally be arranged in a broadside configuration.

By arranging the microphones, such that intra-pair microphones sit closer than inter-pair microphones at least when the headset is in normal operation and intra-pairs in end-fire configurations pointing towards the mouth of a user wearing the headset, the first and the second beamformer can take advantage of the so-called near-field effect to improve the signal-to-noise ratio more at low frequencies (than at higher frequencies) and in addition make it possible to cancel more noise at higher frequencies, avoiding spatial aliasing. The improvement in signal-to-noise ratio may be up to 15 dB. Additionally, the third beamformer can take advantage of the different local noise levels that the different pairs of microphones are exposed to. When the microphone pairs sit on different sides of a person's head, the head may form a wind and/or sound shadow reducing noise level on one side of the person's head. It is a major advantage of the invention that the highly complex problem of designing a single adaptive beamformer operating on all microphone inputs is decomposed into three simple, robust, well-understood dual-microphone beamformers.

In general, different types of microphones with different characteristics may be selected.

A desired signal is a signal that typically represents voice from a speaker within proximity of the microphones or voice appearing from a certain direction relative to the orientation of the microphones. A desired signal may be characterised by being emitted from one or more sound sources having predefined spatial locations with respect to the spatial location of the microphones. Since multiple microphones are used to pick up the desired signal the desired signal may be characterised by a predefined phase and/or amplitude difference among the microphone signal and/or among beamformed signals. A desired signal may also be characterised by a predefined temporal characteristic and/or a predefined phase-/amplitude-frequency characteristic.

A noise signal or simply noise may include turbulence sounds induced by wind occurring at sufficiently high wind speeds and acting on the microphone membranes. Noise may also include background sounds such as tones from machines, sounds from items rattling or chinking, sounds from people talking amongst each other, etc. In some definitions, noise is characterised by being emitted from one or more sound sources that are located at other locations than the desired signal.

The first beamformer and the second beamformer adapt the directional sensitivity gradually or in steps e.g. comprising sensitivities that are at least approximated from the group of the following characteristics: Omni-directional, bi-directional, cardioid, subcardioid, hypercardioid, supercardioid or shotgun. The directional sensitivity may be changed gradually between an omni-directional, a bi-directional and a cardioid characteristic. The first beamformer may be configured as disclosed in WO 2009/132646 which is hereby incorporated by reference for everything disclosed in connection with especially FIG. 1 thereof.

The third beamformer may combine the signals from the first and the second beamformer in accordance with coefficients estimated from noise powers. In case the noise power of the signal from the first beamformer is higher than the noise power of the signal from the second beamformer, the signal from the second beamformer is weighted higher than the signal from the first beamformer and vice versa. The noise level of a signal may be estimated when voice is detected as not present.

The first mutual distance between the microphones of the first pair and the second mutual distance between the microphones of the second pair is shorter than the minimum wavelength of interest in the case of end-fire pairs, depending on the desired directional sensitivity. At and above frequencies with a shorter wavelength than the wavelength of interest, the ability to suppress or cancel noise will diminish due to the effect of spatial aliasing. The distance between the microphone pairs may correspond to the straight-line distance between a person's two ears, which may be about 18-22 cm. The first mutual distance and the second mutual distance may be about 10, 20, or 40 mm for a bandwidth of interest up to 4 KHz.

In general, the apparatus may perform signal processing in a time-domain or in a time-frequency-domain. In the latter case, time-to-frequency transformations are performed on signal blocks of a predefined duration on a running basis. In the time-frequency-domain signals are represented as time-domain samples in a number of frequency bins. Correspondingly, frequency-to-time reconstruction is performed on signals processed in the time-frequency-domain.

In some embodiments the noise reduction unit is configured to perform noise suppression on the combined signal from the third beamformer in response to a noise suppression coefficient; and the noise suppression coefficient is estimated from the microphone signals and/or a beamformed signal. The noise reduction unit is configured as a time-varying filter either in the time-domain or in the time-frequency domain. The noise suppression coefficients may vary over time and determines the time-varying filtering.

The noise suppression coefficient may comprise a first coefficient estimated from the first set of microphone signals and from a/the beamformed signal. The noise suppression coefficient may alternatively or additionally comprise a second coefficient estimated from the second set of microphone signals and from a/the beamformed signal. The noise suppression coefficient may be combined from the first and the second coefficient.

The noise suppression coefficient may be a gain factor of a multiplier in a time-frequency domain or a filter coefficient of a time-domain filter.

In some embodiments the apparatus comprises: a first control branch synthesizing a first noise suppression gain from the first pair of microphone signals and/or the first beamformer; a second control branch synthesizing a second noise suppression gain from the second pair of microphone signals and/or the second beamformer; and a selector configured to dynamically select and/or output the first noise suppression gain or the second noise suppression gain; wherein the noise reduction unit is configured to process the combined signal from the third beamformer in response to the selected and/or output noise suppression gain from the selector.

Thereby it is possible to dynamically select the first or the second noise suppression gain such that it is in accordance with signal quality measures estimated from respective beamformed signal output from a respective beamformer and respective noise suppression gains. This is expedient since the first and the second noise reduction gains may be computed under conditions which are not equally favourable. As a consequence, the noise may not be suppressed equally well and/or the desired signal may not be preserved equally well. For example, the mechanism for computing the first noise suppression gain may have access to signals which lend themselves to easier discrimination of the noise and the desired signal. This condition may arise from the situation where noise is less powerful at the input to the first beamformer due to a user's head shadow causing less wind noise or background noise. The condition may also arise from the situation where the spatial cues employed by the first noise suppression computation are more discriminative.

A hysteresis or threshold may be applied and used as a criterion on whether to enable the selector or not. Thereby it is possible to disable switching when an estimated noise level is below a predefined hysteresis or threshold. The hysteresis or threshold may be in the range of about 1 dB to about 3 dB. Thereby, it is possible to strike a trade-off between (1) achieving lowest output noise level and (2) minimize distortion of a desired signal such as a voice signal.

In some embodiments the selector is configured to operate in response to a first signal quality indicator and a second signal quality indicator; the signal quality indicators are synthesized from a respective beamformed signal processed to reduce noise in response to respective noise reduction gains.

In terms of noise suppression, an important aspect of signal quality is signal-to-noise ratio. As an example, with reference to FIG. 2, when using the beamformed, noise reduced signals as input to Signal Quality Evaluation, signal-to-noise ratio is influenced through $X_L$ and $X_R$. For example, if the signal-to-noise ratio of $X_L$ is greater than that of $X_R$, in cases where $A_L$ and $A_R$ reduce the noise component by the same factor, the signal-to-noise ratio of $A_L X_L$ will be higher than that of $A_R X_R$.

Furthermore, the Signal Quality Evaluation is influence by the qualities of $A_L$ and $A_R$. In some cases, speech is easier distinguishable from noise at one side of the head. A reason is that a user's head may shield the microphones from wind on a lee side of the user's head. Another reason is that the spatial cues employed by the noise suppression computation may be discriminated more clearly on the lee side of the user's head.

The signal quality indicators $P_L$; $P_R$, may be computed from the mean-squared product of the respective noise reduction gains, $A_L$; $A_R$, and the respective beam-formed signals $X_L$; $X_R$. The signal quality indicators may be computed per frequency band or accumulated across all frequency bands.

In some embodiments a beamformed signal, processed to reduce noise in response to respective noise reduction gains, is input to an evaluator that is configured to output a control signal to the selector and thereby control selection; and the evaluator evaluates the beamformed signal, processed to reduce noise in response to respective noise reduction gains, according to a criterion of least power during a time interval when voice activity is detected as not present.

Thereby, the selection of respective noise suppression gains can be performed from an evaluation of the noise conditions (e.g. noise power) at respective sides of a person's head.

Least noise power of the left and the right beamformed, noise reduced signals used as a selection criterion combines a number of quality parameters into a simple computation. As previously mentioned, noise power is a similar measure of signal-to-noise ratio when the microphone inputs are aligned through alignment filters, but it is simpler to compute.

When noise reduction is performed, there is a risk of introducing voice processing artefacts that degrades voice quality. The noise power measure, used in the least noise power criterion, selects for higher voice quality in many cases. When the criterion is based on least power, preference is associated with signals where it is easier to detect all parts of the voice component, especially the low-level parts, which in turn leads to fewer audible instances of voice processing artifacts. A voice activity detector may output a signal indicative of whether voice activity is detected or not. Voice activity may be detected when an amplitude or peak magnitude or power level of one or more microphone signals and/or a beamformed signal exceed a predefined or time-varying threshold. The level of the threshold may be adapted to an estimated noise level.

In some embodiments the noise suppression coefficient is computed to reduce noise by a predetermined, fixed factor.

The predetermined factor may be e.g. 13 dB, 6 dB, 10 dB, 15 dB or another factor. This may be achieved by limiting the noise suppression gain to the predetermined factor.

As an example, an estimated noise level at the output of the first beamformer and the second beamformer may be, say, −30 dB and −20 dB, respectively; the fixed factor may be say 10 dB; and consequently, the estimated noise level after noise suppression is then −40 dB and −30 dB, respectively.

The left and right signal beamformed signals may be matched in level towards the signal of interest, e.g. using alignment filters/gains on the microphones at any point in the signal chain preceding the noise suppression gain selection module. As a beneficial consequence of using fixed noise suppression factors and level-matched left and right channels, noise power computations are conditioned to serve as left and right signal quality measures which reflect the signal-to-noise ratios of the left and right beamformer outputs to a higher degree.

In some embodiments at least one of the first beamformer or the second beamformer is configured to comprise: a first stage that generates a summation signal and a difference signal from the input signals, subject to at least one of the input signals being phase and/or amplitude aligned with another of the input signals with respect to a desired signal; and a second stage that filters the difference signal and generating a filtered signal; wherein the beamformed output signal is generated from the difference between the summation signal and the filtered signal; and wherein the filter is adapted using a least mean square technique to minimize the power of the beamformed output signal.

Thereby the first and/or the second beamformer selectively and adaptively cancel out sound from certain directions.

The filter may have a low-pass characteristic to enhance lower frequency components relative to higher frequency components. The filter may be a bass-boost filter.

Such a beamformer may be configured as disclosed in WO 2009/132646 which is hereby incorporated by reference for everything it discloses.

In some embodiments the third beamformer is configured with a fixed sensitivity with respect to a predefined spatial position relative to the spatial position of the microphones.

A fixed sensitivity means that the third beamformer applies a fixed frequency response with respect to sound emanating from an acoustic source at the predefined spatial position.

The predefined position is located in a predefined way with respect to the spatial position and orientation of the first set of microphones and the second set of microphones. The predefined space is preferably centred about a person's mouth when the apparatus is worn by the person in a normal way.

Beamforming coefficients of the third beamformer may be constrained to sum to a fixed gain e.g. unity gain towards the spatial position. The gain is fixed in the sense that it is not adaptive. However, the gain may be adjusted in connection with calibration or as a preference setting.

The third beamformer may combine the input signals by a linear combination. Alternatively, the signals may be combined by a non-linear combination.

In some embodiments the microphones output digital signals; the apparatus performs a transformation of the digital signals to a time-frequency representation, in multiple frequency bands; and the apparatus performs an inverse transformation of at least the combined signal to a time-domain representation.

The transformation may be performed by means of a Fast Fourier Transformation, FFT, applied to a signal block of a predefined duration. The transformation may involve applying a Hann window or another type of window. A time-domain signal may be reconstructed from the time-frequency representation via an Inverse Fast Fourier Transformation, IFFT.

The signal block of a predefined duration may have duration of 8 ms with 50% overlap, which means that transformations, adaptation updates, noise reduction updates and time-domain signal reconstruction are computed every 4 ms. However, other durations and/or update intervals are possible. The digital signals may be one-bit signals at a many-times oversampled rate, two-bit or three-bit signals or 8 bit, 10, bit 12 bit, 16 bit or 24 bit signals.

In alternative implementations/embodiments, all or parts of the system operate directly in the time-domain. For example, noise suppression may be applied to a time domain signal by means of FIR or IIR filtering, the noise suppression filter coefficients computed in the frequency domain.

In some embodiments the microphones output analogue signals; the apparatus performs analogue-to-digital conversion of the analogue signals to provide digital signals; the apparatus performs a transformation of the digital signals to a time-frequency representation, in multiple frequency bands; and the apparatus performs an inverse transformation of at least the combined signal to a time-domain representation.

In some embodiments the microphones of at least one pair of the set of microphones is arranged in an end-fire configuration oriented towards a position where a person's mouth is expected to be when the apparatus is used by the person. Such a configuration has shown to give good noise cancelling and suppression, e.g., for headsets or hearing aids.

There is also provided a method for processing audio signals from multiple microphones, comprising: receiving a first pair and a second pair of microphone signals from a first pair of microphones and a second pair of microphones, respectively; wherein the first pair of microphones are arranged with a first mutual distance and the second pair of microphones are arranged with a second mutual distance, and wherein the first pair of microphones are arranged at a distance from the second pair of microphones that is greater than the first mutual distance and the second mutual distance at least when the apparatus is in normal operation; performing first beamforming and second beamforming on the first pair of microphone signals and the second pair of microphone signals to output respective beamformed signals; adapting the spatial sensitivity by a respective pair of microphones as measured in a respective beamformed signal such that spatial sensitivity is adapted to suppress noise relative to a desired signal; performing third beamforming to dynamically combine the signals output from the first beamforming and the second beamforming into a combined signal; wherein the signals are combined such that noise energy in the combined signal is minimized while a desired signal is preserved; and performing noise reduction to process the combined signal from the third beamformer and output the combined signal such that noise is reduced.

There is also provided a computer program product, e.g. stored on a computer-readable medium such as a DVD, comprising program code means adapted to cause a data processing system to perform the steps of the method, when said program code means are executed on the data processing system.

There is also provided a computer data signal, e.g. a download signal, embodied in a carrier wave and representing sequences of instructions which, when executed by a processor, cause the processor to perform the steps of the method.

Here and in the following, the terms 'processing means' and 'processing unit' are intended to comprise any circuit and/or device suitably adapted to perform the functions described herein. In particular, the above term comprises general purpose or proprietary programmable microprocessors, Digital Signal Processors (DSP), Application Specific Integrated Circuits (ASIC), Programmable Logic Arrays (PLA), Field Programmable Gate Arrays (FPGA), special purpose electronic circuits, etc., or a combination thereof.

BRIEF DESCRIPTION OF THE FIGURES

The above and/or additional objects, features and advantages of the present invention will be further elucidated by the following illustrative and non-limiting detailed description of embodiments of the present invention, with reference to the appended drawings, wherein.

DETAILED DESCRIPTION

In the following description, reference is made to the accompanying figures, which show, by way of illustration, how the invention may be practiced.

Figure 1:
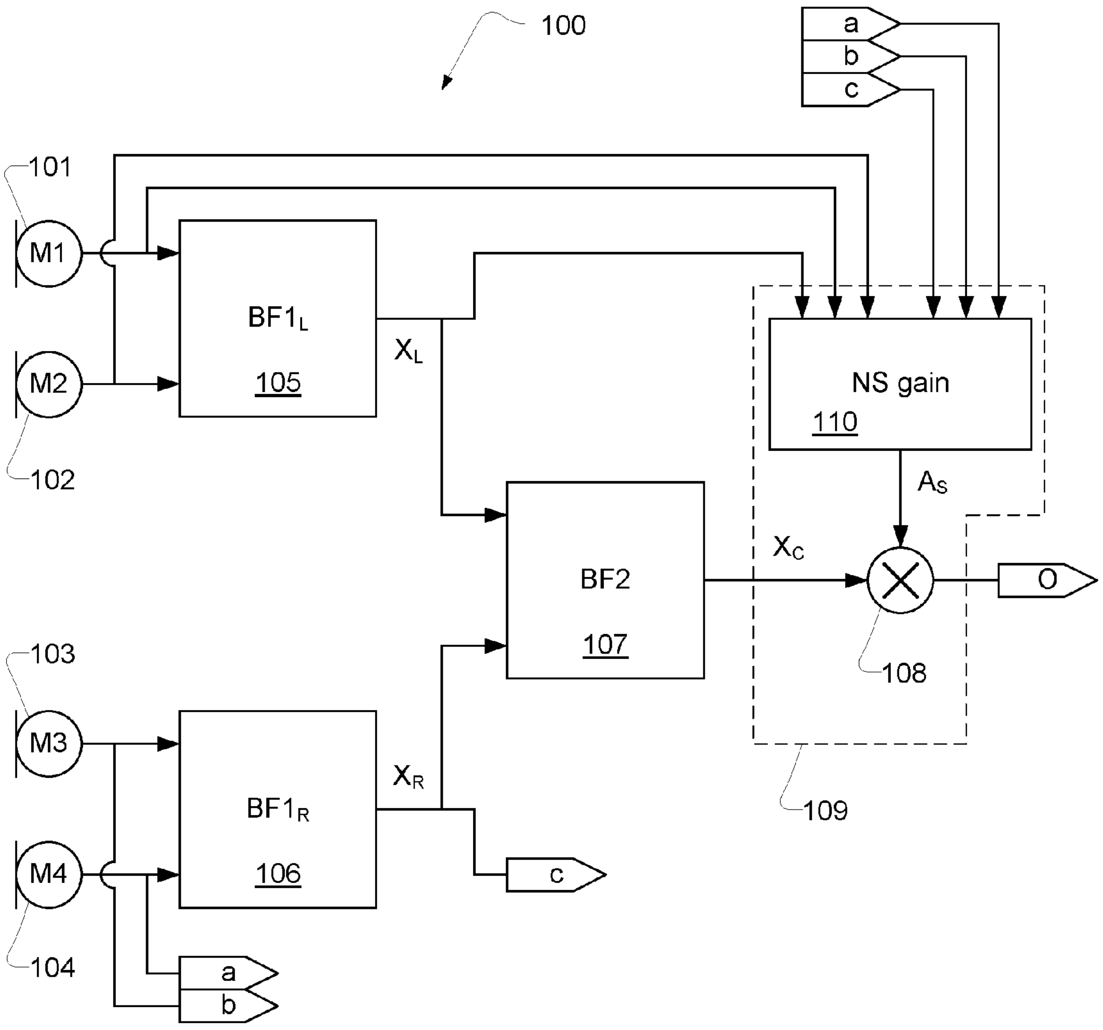
FIG. 1 shows a block diagram of a signal processor.

FIG. 1 shows a block diagram of a signal processor and a first and second pair of microphones. The first set of microphones, 101 and 102, and the second set of microphones, 103 and 104, are arranged with an intra-pair distance between the microphones that is relatively short compared to the microphone pairs inter-distance, between the pairs of microphones. The signal processor is designated by reference numeral 100.

The first pair of microphones 101 and 102 outputs a first microphone signal pair input to a first beamformer 105 and the second pair of microphones 103 and 104 outputs a second microphone signal pair, which is input to a second beamformer 106. The first beamformer 105 and the second beamformer 106 outputs respective output signals $X_L$ and $X_R$.

The first beamformer 105 and the second beamformer 106 are each configured to adapt their spatial sensitivity. The spatial sensitivity is adapted to cancel or suppress noise relative to a desired signal. The first beamformer and the second beamformer may be configured as disclosed in WO 2009/132646.

The third beamformer 107 is configured to dynamically combine the signals, $X_L$; $X_R$, output from the first beamformer 105 and the second beamformer 106 into a combined signal $X_C$. The combined signal $X_C$ can be expressed by the following expression:

$$X_C = G_L X_L + G_R X_R$$

Where $G_L$ and $G_R$ represent transfer functions from a first input at which $X_L$ is received and from a second input at which $X_R$ is received, respectively. The above expression relies on a frequency domain representation; $X_L$ and $X_R$ are complex numbers. An equivalent representation exists for a time-domain representation. The third beamformer is configured to adjust real or complex $G_L$ and $G_R$ dynamically to output $X_C$ with a lowest noise level while preserving a desired signal.

The following expression is an example of how real $G_L$, $G_R$ may be computed:

$$\hat{G}_L = \frac{\langle |X_R|^2 \rangle - Re\langle X_L X_R^* \rangle}{\langle |X_L - X_R|^2 \rangle}$$

$$\hat{G}_R = \hat{G}_L - 1$$

where Re is the real part of a complex number, .*, <•< and |•| represent complex conjugate, averaging across a time interval and absolute value, respectively.

The above expressions for real $\hat{G}_L$ and $\hat{G}_R$ are solutions to a mean squares cost function subject to a constraint:

$$\hat{G}_L = \underset{G_L}{\operatorname{argmin}} \langle |X_C|^2 \rangle$$

subject to:

$$\hat{G}_L + \hat{G}_R = 1$$

That is, the mean-squares of $X_C$ are minimized as a function of real $G_L$, subject to a constraint. The constraint ensures that the desired signal is favoured over signals from at least some other locations.

In some embodiments matching filters are inserted between the microphones and the inputs to the beamformers of the first stage i.e. in the shown embodiment the first and the second beamformer. Thereby filtering the input signals to the first and the second beamformers so that the desired signal component is sufficiently identical in all the inputs, i.e., with respect to phase and amplitude. The filters compensate for variations in acoustic path of the desired signal to the microphones as well as variations in microphone sensitivities or other variations. Such matching filters may also be denoted alignment filters and matching may be denoted alignment. As a result of the input alignment with respect to the desired source, the output desired signal component of the first and second beamformers are similarly identical due to the inbuilt constraints (e.g. as described in WO 2009/132646). That is, the inputs to the third beamformer are sufficiently identical with respect to the desired signal component. As a consequence, the $\hat{G}_L+\hat{G}_R=1$ constraint leads to the output and inputs of the third beamformer being sufficiently identical with respect to the desired signal.

One of the inputs may be chosen as a reference for microphone alignment. For example, one of the alignment filters may be configured to produce an all-pass characteristic; the other alignment filters are configured accordingly. As a result, the outputs of each of the first stage beamformers with respect to the desired signal are sufficiently similar and also similar to the reference input.

The microphone alignment filters may be pre-configured by assuming and compensating for a known acoustical relation between the origin of the desired signal and the microphones and using microphones with very small variations in sensitivities. The microphone sensitivities may be estimated in a calibration step at the time of production. The microphone alignment filters may be estimated while the device is in operation: when activated by a voice or noise activity detector, the alignment filters are estimated by, e.g., a least squares technique.

Constraining the beamformer with respect to the desired signal may be equivalently achieved by integrating the microphone alignment filters directly into one or more of the beamformers' calculations, or, alternatively at the outputs of the first and second beamformers.

When the input signals ($X_L$; $X_R$) are combined in this way, the input signal that exhibits the lowest noise level is emphasized over the other one.

The above expression for computing $G_L$ and $G_R$ is at least to some extent resistant to the influence of the desired signal and may work sufficiently well without any voice-activity detector, VAD.

The below expression is an alternative and is somewhat less resource demanding to compute, but is advantageously used in combination with a voice-activity detector, VAD:

$$\tilde{G}_L = \frac{\langle |X_R|^2 \rangle}{\langle |X_R|^2 \rangle + \langle |X_L|^2 \rangle}$$

$$\tilde{G}_R = \tilde{G}_L - 1$$

Where $X_R$ and $X_L$ are complex representations of the respective signals. This expression is subject to similar minimization and constraint as mentioned above but assumes that noise components in $X_R$ and $X_L$ are uncorrelated. In this case the voice-activity detector is applied to discard signal portions of $X_R$ and $X_L$ wherein voice is present for the purpose of estimating $G_L$ and $G_R$. Such a weighting rule was disclosed in U.S. Pat. No. 7,206,421 B1 for a multi-microphone input.

For more robust performance, $G_L$ and $G_R$ may be constrained further to an interval, say, between 0 and 1.

In general, it should be noted that the estimated position of the source emitting the desired signal may be pre-configured and locked to an expected position relative to the positions of the microphones. This could be the case for a headset, wherein the position of a person's mouth may be sufficiently well-defined when the headset is worn in a normal position. In other cases, the apparatus may comprise a tracker that estimates the position of the source of the desired signal from, e.g., phase and/or amplitude differences in the signals from one, two or more microphone pairs or sets of more than two microphones. This could be the case for a speakerphone or a hands-free set for a communications device in, e.g., a car.

The combined signal, $X_C$, is input to a noise suppression unit 109 that computes a noise suppression gain, $A_S$, from the beamformed signals $X_L$ and $X_R$. Additionally, the noise suppression unit 109 may include the microphone signals from one or more of the microphones 101, 102, 103, 104 in computing the noise suppression gain, $A_S$. The signals from M3 and M4 and the signal $X_R$ output from the beamformer 106 are labelled 'a', 'b' and 'c' and are input to the noise suppression unit 109 as indicated by respective labels.

Computation of the noise suppression gain, $A_S$, is described further below.

In the shown embodiment, the noise suppression gain, $A_S$, is applied to the combined signal, $X_C$, by a multiplier 108. A signal output from the multiplier is a reproduced audio signal comprising beamformed and noise suppressed signal components picked up by the microphones. Label '0' designates output from the signal processor. The output may be subject to further signal processing, amplification and/or transmission.

Figure 2:
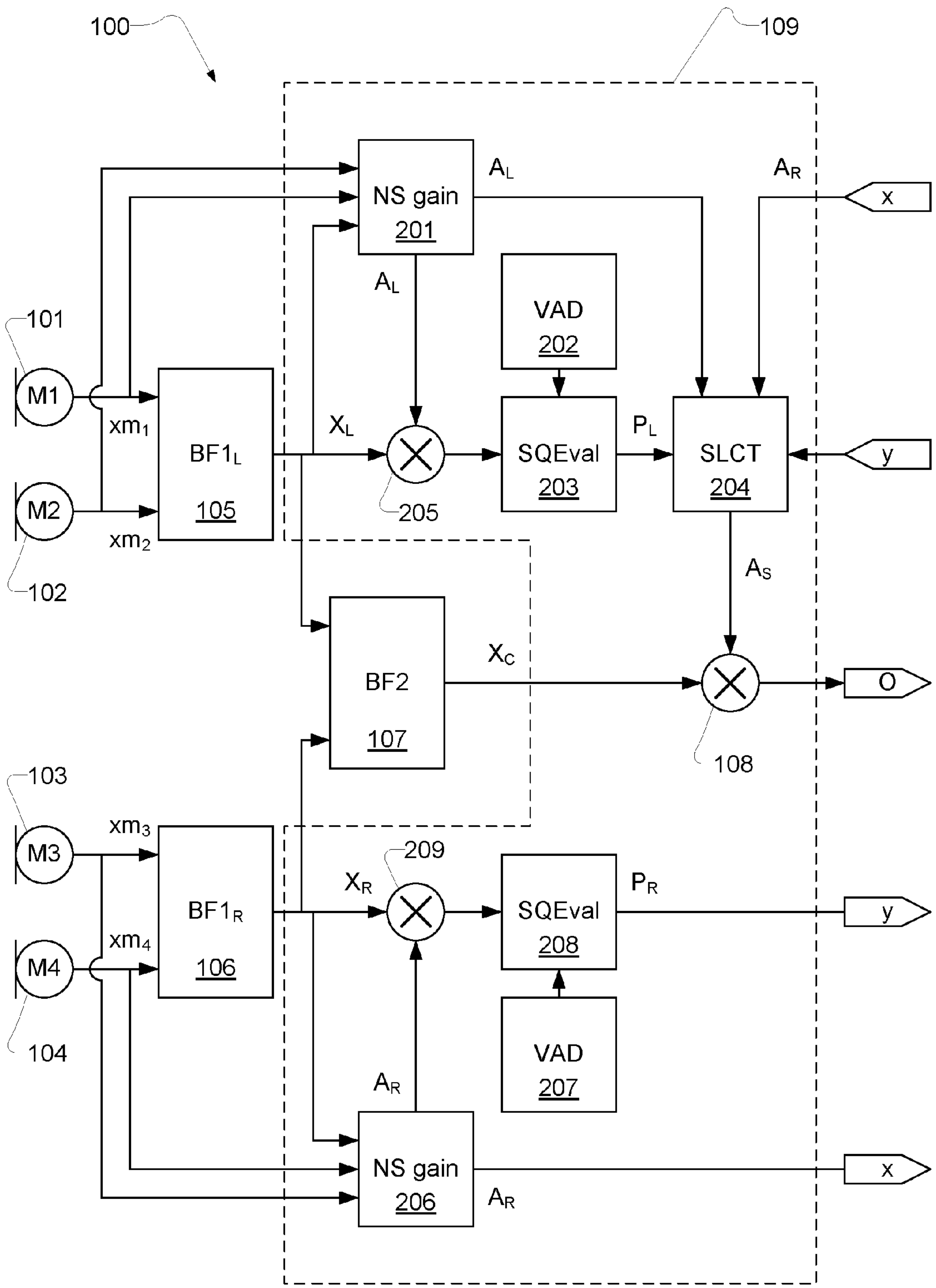
FIG. 2 shows a more detailed block diagram of the signal processor.

FIG. 2 shows a more detailed block diagram of the signal processor. It is shown that the noise suppression gain, $A_S$, is selected as either a first or left noise suppression gain, $A_L$, or a second or right noise suppression gain, $A_R$. The left noise suppression gain, $A_L$, is computed from the beamformed signal $X_L$ and/or the microphone signals $xm_1$ and/or $xm_2$. Correspondingly, the right noise suppression gain, $A_R$, is computed from the beamformed signal $X_R$ and/or the microphone signals $xm_3$ and/or $xm_4$.

$A_L$ is applied to $X_L$ via multiplier 205 and $A_R$ is applied to $X_R$ via multiplier 209. Respective outputs of the multipliers 205 and 209 are input to respective signal quality evaluators 203 and 208. The inputs may be interpreted as left and right noise-reduced, beamformed signals.

The signal quality evaluators 203 and 208 may evaluate the signal quality of the signals output from the multipliers 205 and 209 according to a criterion of signal-to-noise ratio. Alternatively, signal quality may be evaluated according to a criterion of noise signal power during a time interval when voice activity is detected as not present. This may be facilitated by applying the microphone alignment filters to render the desired signal component sufficiently identical at all beamformer inputs and outputs. In this case, signal-to-noise ratio and noise power are similar measures of signal quality. The signal quality evaluators output signals $P_L$ and $P_R$ that selects either $A_L$ or $A_R$ via a selector 204. $A_S$, which is output from the selector represents the selected noise suppression gain and it is applied to $X_C$ via a multiplier 108.

Signals $P_L$ and $P_R$ and hence the signal quality evaluators 203 and 208 may be defined as power computations on the noise component of the signals received as inputs. For example, $P_L$ may be defined as the mean square of the beamformed, noise-reduced input during noise-only intervals. Averaging may be performed across a suitable time interval, e.g., 100 ms or 1 s, and across a suitable frequency interval, e.g. 0-8000 Hz.

The selector 204 may be configured to select $A_L$ when $P_L$ is less than $P_R$ and conversely select $A_R$ when $P_L$ is larger than $P_R$. Voice activity detectors 202 and 207 output signals to the signal quality evaluators 203 and 208, respectively, indicative of whether voice is detected.

A voice activity detector, VAD, of a single-input type, may be configured to estimate a noise floor level, N, by receiving an input signal and computing a slowly varying average of the magnitude of the input signal. A comparator may output a signal indicative of the presence of a voice signal when the magnitude of the signal temporarily exceeds the estimated noise floor by a predefined factor of, say, 10 dB. The VAD may disable noise floor estimation when the presence of voice is detected. Such a voice detector works when the noise is quasi-stationary and when the magnitude of voice exceeds the estimated noise floor sufficiently. Such a voice activity detector may operate at a band-limited signal or at multiple frequency bands to generate a voice activity signal aggregated from multiple frequency bands. When the voice activity detector works at multiple frequency bands, it may output multiple voice activity signals for respective multiple frequency bands.

A voice activity detector, VAD, of a multiple-input type, may be configured to compute a signal indicative of coherence between multiple signals. For example, the voice signal may exhibit a higher level of coherence between the microphones due to the mouth being closer to the microphones than the noise sources. Other types of voice activity detectors are based on computing spatial features or cues such as directionality and proximity, and, dictionary approaches decomposing signal into codebook time/frequency profiles.

A noise suppression gain designated $G_{NS}$ or $A_L$ or $A_R$ may be computed from the following expression:

$$G_{NS} = \frac{|X|^2}{|X|^2 + P_N F}$$

Wherein $P_N$ is the square of the estimated noise floor level at a time instance t; $|X|^2$ is the square of the input signal at the time instance t; and F is a factor, e.g., a factor of 10. The noise suppression gain affects an input signal via a multiplier, if applied in a frequency domain.

Thus, on the one hand, if the noise floor level is very low, $G_{NS}$ becomes 1 when voice is significantly present. On the other hand, if voice is absent or the noise level rises, $G_{NS}$ moves to values less than 1 and consequently a suppression of the input signal. The factor F is selected to set how aggressively the input signal should be suppressed.

In respect of the above description of a voice-activity detector and noise suppression gain, its input signal(s) may be any of the microphone signals and/or output from the first beamformer and/or second beamformer and/or third beamformer.

In general, a way to estimate the signal and noise relation is based on tracking the noise floor, wherein voice or noisy voice is identified by signal parts significantly exceeding the noise floor level. Noise levels may, e.g., be estimated by minimum statistics as in [R. Martin, "Noise Power Spectral Density Estimation Based on Optimal Smoothing and Minimum Statistics," Trans. on Speech and Audio Processing, Vol. 9, No. 5, July 2001], where the minimum signal level is adaptively estimated.

Other ways to identify signal and noise parts are based on computing multi-microphone/spatial features such as directionality and proximity [O. Yilmaz and S. Rickard, "Blind Separation of Speech Mixtures via Time-Frequency Masking", IEEE Transactions on Signal Processing, Vol. 52, No. 7, pages 1830-1847, July 2004] or coherence [K. Simmer et al., "Post-filtering techniques." Microphone Arrays. Springer Berlin Heidelberg, 2001. 39-60]. Dictionary approaches decomposing signal into codebook time/frequency profiles may also be applied [M. Schmidt and R. Olsson: "Single-channel speech separation using sparse non-negative matrix factorization," Interspeech, 2006].

In general, noise suppression may be implemented as described in [Y. Ephraim and D. Malah, "Speech enhancement using optimal non-linear spectral amplitude estimation," in Proc. IEEE Int. Conf. Acoust. Speech Signal Processing, 1983, pp. 1118-1121] or as described elsewhere in the literature on noise suppression techniques. Typically, a time-varying filter is applied to the signal. Analysis and/or filtering are often implemented in a frequency transformed domain/filter bank, representing the signal in a number of frequency bands. At each represented frequency, a time-varying gain is computed depending on the relation of estimated desired signal and noise components e.g. when the estimated signal-to-noise ratio exceeds a pre-determined, adaptive or fixed threshold, the gain is steered toward 1. Conversely, when the estimated signal-to-noise ratio does not exceed the threshold, the gain is set to a value smaller than 1. The labels designated 'x' and 'y' connect the respective signals: x-to-x and y-to-y.

Figure 3:
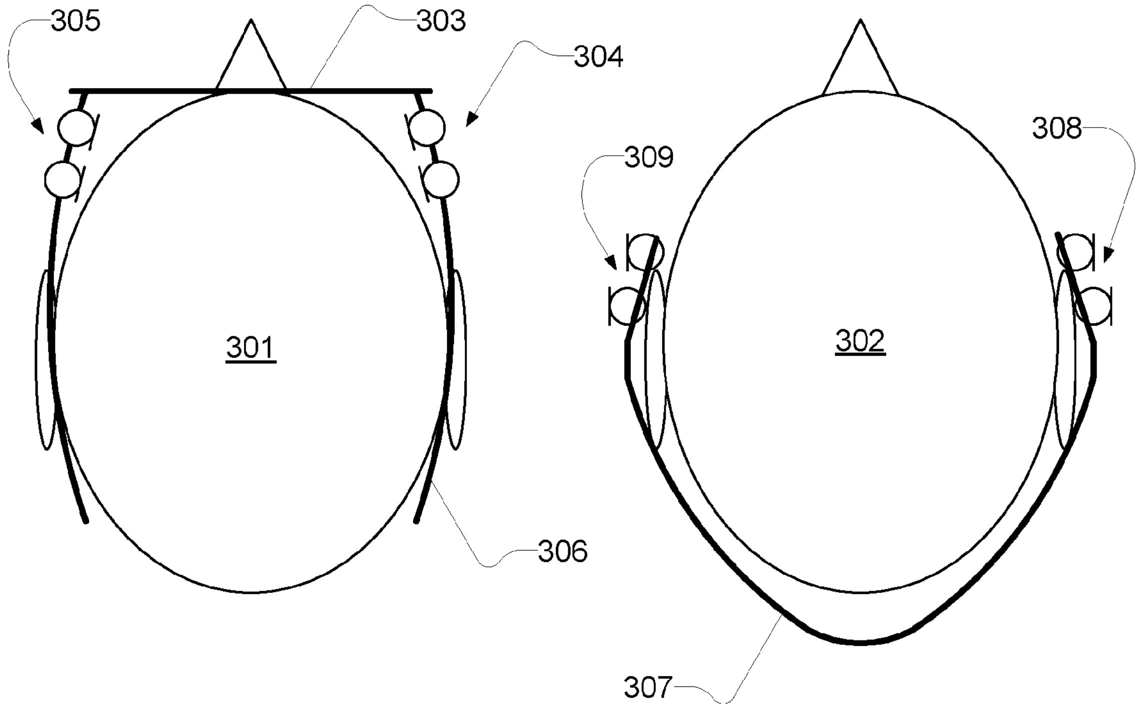
FIG. 3 shows different configurations of an apparatus with multiple microphones.

FIG. 3 shows different configurations of an apparatus with multiple microphones. On the left-hand side, a spectacle frame 303 with bows 306 are configured with two sets of microphones 304 and 305. On the right-hand side, a flexible neckband 307 is configured with two sets of microphones 308 and 309. Reference numeral 301 designates the head of a person wearing the spectacle frame 303 and reference numeral 302 designates the head of a person wearing the neckband 307.

The microphones may be arranged in a so-called end-fire configuration wherein the microphones of a respective pair or set of microphones sit on a line that intersects with or passes close to a position of a source of a desired signal. The position may be a position of the person's mouth opening or a position in proximity of the person's mouth opening. In an end-fire configuration the microphones of a microphone pair sit on a straight line intersecting the position of the source of the desired signal. Such a configuration is found to be suitable for effectively suppressing or cancelling noise from sources located elsewhere when the apparatus is a headset, hearing aid or the like.

In alternative configurations, a so-called broadside configuration for the microphone positions is used. In a broadside configuration the microphones of a microphone pair sit on a straight line at an equal distance to the position of the source of the desired signal.

In still alternative configurations, the microphones of a microphone pair sit on a line inclined e.g. at 5°, 10°, 45° relative to a direction from the microphone pair to the position of the source of the desired signal, thereby providing a configuration that may be more practically suitable.

Generally, in the above it is assumed that so-called digital microphones outputting digital signals are used. However, analogue microphones in conjunction with an analogue-to-digital converter or any other transduction from the sound field to a sampled domain could be used. The microphones are typically embodied in so-called capsules with a diameter in the range of typically 3 mm to 5 mm or 6 mm.

In general, a beamformer may receive signals from more than a pair of microphones. A beamformer, e.g., a first stage beamformer, may receive microphone signals from 3, 4 or more microphones. The first stage may comprise more than the first and the second beamformer; the first stage may comprise, e.g., 3, 4 or more beamformers.

It should be noted that in hearing aids and in assistive hearing devices beamforming is configured for far-field beamforming in contrast to near-field beamforming, which is employed in headsets.

Additionally, beamforming cannot produce a net positive effect unless the background noise sufficiently exceeds the microphone noise. This is due to the so-called white-noise-gain of a beamformer, wherein uncorrelated (between inputs) noise such as microphone noise, wind noise and quantization noise are amplified by the beamformer.

For effective beamforming towards a far-field source, a headroom of about 30 dB is needed at low frequencies, whereas a significantly lower headroom of about 15 dB may suffice for beamforming towards near-field sources.

Thus, at times when the background noise is not loud enough, in a range of frequencies, beamforming in that range of frequencies must be disabled to avoid a net amplification of noise.

Due to the stricter headroom requirement when the source is in the far-field, the far-field beamformer must typically be disabled most of the time at lower frequencies.

On the contrary, a near-field beamformer that beamforms towards a near-field source typically run unimpeded most of the time. As a consequence, the third beamformer operates surprisingly more effectively when the first beamformer and the second beamformer are configured as near-field beamformers. Thus, since the first and the second beamformer run unimpeded most of the time, the likelihood that there is a significant difference in signal-to-noise ratio between the output of the first and the output of the second beamformer is higher. Therefore, since the third beamformer selectively combines the output of the first and the output of the second beamformer the signal-to-noise ratio is significantly improved. This is due to the fact that microphone noise (with a near-field beamformer) will not as often (as a far-field beamformer) cause the first and second beamformers to be effectively disabled.

A major advantage is that the claimed headset and method combines the advantage of end-fire array beamforming towards a near-field source, which is a user's mouth, with the benefit of the noise and wind shadowing effect of the user's head to reach unforeseen levels of noise suppression. This greatly improves the quality of a picked up speech signal in e.g. an outdoor environment—and thus the quality of speech comprehension at a remote end of e.g. a phone call.

A beamformer for a headset (i.e. a near-field beamformer) is configured to focus spatially on sources (such as a user's mouth) within a range of less than 25 cm±10% or less than or about 20 cm±10% or less than or about 18 cm±10% from the first pair of microphones and/or the second pair of microphones. In connection therewith the microphones of the first pair of microphones are arranged with a first mutual distance and the microphones of the second pair of microphones are arranged with a second mutual distance. The first mutual distance and/or the second mutual distance are in the range of about 5 mm±10% to about 20 mm±10% or about 35 mm±10% e.g. about 10 mm or 15 mm.

Near-field beamforming focussed on the mouth of a user wearing the headset means that a beamformer is focussed on the location of the opening of the user's mouth or in proximity thereof e.g. a few centimeters such as 2, 3, 4, 5, 10 or 15 cm in front of the mouth.

In more detail a generalized and idealized two-microphone beamformer can be described by the following expression, in a frequency-domain (complex) representation:

$$Z=(X_1\Delta_2\cdot X_2)\cdot EQ$$

Wherein $X_1$ and $X_2$ are microphone signals from a front and a rear microphone, respectively, in an end-fire microphone configuration; $\Delta_2$ is a time delay (phase modification) which determines the directional characteristic (e.g. cardiod or bi-directional) of the beamformer; EQ determines a frequency characteristic at the output of the beamformer; and Z is the beamformed output. It is assumed that a beamformer represented by the expression receives its input from matched microphones.

The beamformer's response to a source of interest is now investigated. In continuation thereof $X_1$ and $X_2$ is expressed by a common source signal S from a common source and respective transfer functions $B_1$ and $B_2$ from the common source to the microphones:

$$X_1=B_1\cdot S$$

$$X_2=B_2\cdot S$$

Without loss of generality, we now specify that the beamformer should exhibit the same response towards the source as the first microphone:

$$Z=B_1\cdot S$$

Then:

$$EQ = \frac{1}{\left(1 - \Delta_2 \cdot \left(\frac{B_2}{B_1}\right)\right)}$$

Which yields the following for a far-field beamformer:

$$\left|\frac{B_2}{B_1}\right| \cong 1$$

since the source is in the far field. As can be seen from the below expression, EQ increases for low frequencies since the denominator approaches zero. This in turn yields a very high microphone noise gain.

EQ for a far-field beamformer can thus be expressed in the following way:

$$EQ_{FF} = \frac{1}{(1 - \Delta_2 \cdot \Delta_{12})}$$

Wherein $\Delta_{12}$ is a time delay (i.e. a phase modification).

For a near-field beamformer the absolute value of the ratio between the transfer function, $B_2$, from the near-field source to one of the microphones in a microphone pair and the transfer function, $B_1$, from the near-field source to the other of the microphones in a microphone pair equals a constant a (in a frequency domain notation or complex notation), that is:

$$\left|\frac{B_2}{B_1}\right| = a$$

since the source e.g. a user's mouth is within short range of the microphones, e.g. within 30 cm; wherein the microphones of a microphone pair sits much closer e.g. closer than 25 mm apart e.g. 10 mm apart.

EQ for a near-field beamformer can be expressed in the following way:

$$EQ_{NF} = \frac{1}{(1 - \Delta_2 \cdot \Delta_{12} \cdot a)}$$

Wherein the value of a is less than 1 and greater than 0; $0<a<1$. The value of a depends on the path from a user's mouth to a pair of microphones. An end-fire configuration of the pair of microphones give a relatively low value of a. The value of a may be e.g. about 0.7±10% or in the range 0.4 to 0.9. The value of a may be about that value or in that range for a frequency range of interest e.g. a frequency range from about 500 Hz±10% or 800 Hz±10% to about 4 KHz±10% or 8 KHz±10% or a wider or narrower range of frequencies. As can be seen from the expression, $EQ_{NF}$ is smaller than $EQ_{FF}$ at lower frequencies due to a. This in turn yields a lower microphone noise gain and thus a wider range of background noises where the beamformer will improve the signal to noise-ratio.

The invention claimed is:

1. A headset configured to process audio signals from a first pair and a second pair of microphones arranged in a respective first and a second end-fire configuration aimed towards the mouth of a user wearing the headset in a normal position, comprising:

a first pair of microphones outputting a first pair of microphone signals and a second pair of microphones outputting a second pair of microphone signals; wherein the first pair of microphones are arranged with a first mutual distance and the second pair of microphones are arranged with a second mutual distance, and wherein the first pair of microphones are arranged at a distance from the second pair of microphones that is greater than the first mutual distance and the second mutual distance at least when the headset is in normal operation;

a first beamformer and a second beamformer configured to respectively receive the first pair and second pair of microphone signals and perform respective near-field beamforming focussed on the mouth of a user wearing the headset;

a third beamformer configured to dynamically combine beamformed signals ($X_L$; $X_R$) output from the first beamformer and the second beamformer into a combined signal ($X_C$) by weighing; wherein the third beamformer computes a respective noise level of the signals ($X_L$; $X_R$) and weighs the signal with a lowest noise level among the signals ($X_L$; $X_R$) with a highest weight into the combined signal;

a noise reduction unit configured to filter the combined signal ($X_C$) from the third beamformer by a time-varying filter.

2. A headset according to claim 1, wherein the noise reduction unit is configured to perform noise suppression on the combined signal ($X_C$) from the third beamformer in response to a noise suppression gain ($A_L$; $A_R$); and wherein the noise suppression gain ($A_L$; $A_R$) is estimated from one or more of microphone signals among the microphone signals of the pairs of microphone signals or one or more of the beamformed signals ($X_L$; $X_R$).

3. A headset configured to process audio signals from multiple microphones arranged in a first and a second end-fire configuration aimed towards the mouth of a user wearing the headset in a normal position, comprising:

a first pair of microphones outputting a first pair of microphone signals and a second pair of microphones outputting a second pair of microphone signals; wherein the first pair of microphones are arranged with a first mutual distance and the second pair of microphones are arranged with a second mutual distance, and wherein the first pair of microphones are arranged at a distance from the second pair of microphones that is greater than the first mutual distance and the second mutual distance at least when the headset is in normal operation;

a first beamformer and a second beamformer configured to receive pair of microphone signals and perform near-field beamforming focussed on the mouth of a user wearing the headset;

a third beamformer configured to dynamically combine the signals ($X_L$; $X_R$) output from the first beamformer and the second beamformer into a combined signal ($X_C$) by weighing; wherein the third beamformer computes a respective noise level of the signals ($X_L$; $X_R$) and weighs the signal with a lowest noise level among the signals ($X_L$; $X_R$) with a highest weight into the combined signal;

a noise reduction unit configured to filter the combined signal ($X_C$) from the third beamformer by a time-varying filter and further including:

a first control branch synthesizing a first noise suppression gain ($A_L$) from the first pair of microphone signals and/or a signal from the first beamformer;

a second control branch synthesizing a second noise suppression gain ($A_R$) from the second pair of microphone signals and/or a signal from the second beamformer;

a selector configured to dynamically select and/or output the first noise suppression gain ($A_L$) or the second noise suppression gain, ($A_R$);

wherein the noise reduction unit is configured to filter the combined signal from the third beamformer in response to the selected and/or output noise suppression gain ($A_S$) from the selector.

4. A headset according to claim 3, wherein the selector is configured to operate in response to a first signal quality indicator ($P_L$) and a second signal quality indicator ($P_R$); and wherein the first signal quality indicator ($P_L$) and the second signal indicator ($P_R$) are synthesized from a respective beamformed signal ($X_L$; $X_R$).

5. A headset according to claim 3, wherein a beamformed signal ($X_L$; $X_R$), processed to reduce noise in response to respective noise suppression gains ($A_L$; $A_R$) and then input to an evaluator that is configured to output a signal quality indicator ($P_L$; $P_R$) to the selector and thereby control selection; and wherein the evaluator evaluates the beamformed signal ($X_L$; $X_R$), in response to respective noise suppression gains ($A_L$; $A_R$), according to a criterion of least power during a time interval when voice activity is detected as not present.

6. A headset according to claim 2, wherein the noise suppression gain ($A_L$; $A_R$) is computed to reduce noise by a predetermined, fixed factor.

7. A headset configured to process audio signals from multiple microphones arranged in a first and a second end-fire configuration aimed towards the mouth of a user wearing the headset in a normal position, comprising:

a first pair of microphones outputting a first pair of microphone signals and a second pair of microphones outputting a second pair of microphone signals; wherein the first pair of microphones are arranged with a first mutual distance and the second pair of microphones are arranged with a second mutual distance, and wherein the first pair of microphones are arranged at a distance from the second pair of microphones that is greater than the first mutual distance and the second mutual distance at least when the headset is in normal operation;

a first beamformer and a second beamformer configured to receive pair of microphone signals and perform near-field beamforming focussed on the mouth of a user wearing the headset;

a third beamformer configured to dynamically combine the signals ($X_L$; $X_R$) output from the first beamformer and the second beamformer into a combined signal ($X_C$) by weighing; wherein the third beamformer computes a respective noise level of the signals ($X_L$; $X_R$) and weighs the signal with a lowest noise level among the signals ($X_L$; $X_R$) with a highest weight into the combined signal;

a noise reduction unit configured to filter the combined signal ($X_C$) from the third beamformer by a time-varying filter, and wherein at least one of the first beamformer or second beamformer is configured to comprise:

a first stage that generates a summation signal and a difference signal from input signals, subject to at least one of the input signals being phase and/or amplitude aligned with another of the input signals with respect to a desired signal; and a second stage that filters the difference signal and generating a filtered signal;

wherein the beamformed signal ($X_L$; $X_R$) is generated from the difference between the summation signal and the filtered signal; and wherein filtering is adapted using a least mean square technique to minimize the power of the beamformed signal ($X_L$; $X_R$).

8. A headset according to claim 1, wherein the third beamformer is configured with a fixed sensitivity with respect to a predefined spatial position relative to the spatial position of the microphones.

9. A headset according to claim 1, wherein the microphones output digital signals;

wherein the headset performs a transformation of the digital signals to a time-frequency representation, in multiple frequency bands; and wherein the headset performs an inverse transformation of at least the combined signal to a time-domain representation.

10. A headset according to claim 1, wherein the microphones output analogue signals;

wherein the headset performs analogue-to-digital conversion of the analogue signals to provide digital signals;

wherein the headset performs a transformation of the digital signals to a time-frequency representation, in multiple frequency bands; and wherein the headset performs an inverse transformation of at least the combined signal to a time-domain representation.

11. A headset configured to process audio signals from multiple microphones arranged in a first and a second end-fire configuration aimed towards the mouth of a user wearing the headset in a normal position, comprising:

a first pair of microphones outputting a first pair of microphone signals and a second pair of microphones outputting a second pair of microphone signals; wherein the first pair of microphones are arranged with a first mutual distance and the second pair of microphones are arranged with a second mutual distance, and wherein the first pair of microphones are arranged at a distance from the second pair of microphones that is greater than the first mutual distance and the second mutual distance at least when the headset is in normal operation;

a first beamformer and a second beamformer configured to receive pair of microphone signals and perform near-field beamforming focussed on the mouth of a user wearing the headset;

a third beamformer configured to dynamically combine the signals ($X_L$; $X_R$) output from the first beamformer and the second beamformer into a combined signal ($X_C$) by weighing; wherein the third beamformer computes a respective noise level of the signals ($X_L$; $X_R$) and weighs the signal with a lowest noise level among the signals ($X_L$; $X_R$) with a highest weight into the combined signal;

a noise reduction unit configured to filter the combined signal ($X_C$) from the third beamformer by a time-varying filter, and wherein an absolute value of the ratio between the transfer function ($B_2$) from the user's mouth to one of the microphones in the first or second microphone pair and the transfer function ($B_1$) from the user's mouth to the other of the microphones in the respective first or second microphone pair substantially equals a constant (a), wherein a is less than 0.9, at least within a frequency range of interest.

12. A method for processing audio signals from multiple microphones arranged in a headset, comprising:

receiving a first pair and a second pair of microphone signals from a first pair of microphones and a second pair of microphones, respectively; wherein the first pair of microphones are arranged with a first mutual distance and the second pair of microphones are arranged with a second mutual distance, and wherein the first pair of microphones are arranged at a distance from the second pair of microphones that is greater than the first mutual distance and the second mutual distance at least when the headset is in normal operation;

performing first near-field beamforming and second near-field beamforming on the first pair of microphone signals and the second pair of microphone signals and focussed on the mouth of a user wearing the headset in a normal position to output respective beamformed signals ($X_L$; $X_R$);

performing third beamforming to dynamically combine the signals ($X_L$; $X_R$) output from the first near-field beamforming and the second near-field beamforming into a combined signal ($X_C$) by weighing; wherein the third beamforming computes a respective noise level of the signals ($X_L$; $X_R$) and weighs the signal with a lowest noise level among the signals ($X_L$; $X_R$) with a highest weight into the combined signal ($X_C$);

performing noise reduction by filtering the combined signal ($X_C$) from the third beamforming by a time-varying filter.

13. A headset according to claim 1 wherein the noise level of a signal is estimated when voice activity is detected as not present.

* * * * *